US009272158B2

(12) United States Patent
Khizroev et al.

(10) Patent No.: US 9,272,158 B2
(45) Date of Patent: Mar. 1, 2016

(54) METHOD FOR NON-INVASIVE BRAIN STIMULATION

(71) Applicant: THE FLORIDA INTERNATIONAL UNIVERSITY BOARD OF TRUSTEES, Miami, FL (US)

(72) Inventors: Sakhrat Khizroev, Coral Gables, FL (US); Madhavan P. N. Nair, Coral Gables, FL (US)

(73) Assignee: THE FLORIDA INTERNATIONAL UNIVERSITY BOARD OF TRUSTEES, Miami, FL (US)

(*) Notice: Subject to any disclaimer, the term of this patent is extended or adjusted under 35 U.S.C. 154(b) by 338 days.

(21) Appl. No.: 13/900,305

(22) Filed: May 22, 2013

(65) Prior Publication Data

US 2013/0317279 A1 Nov. 28, 2013

Related U.S. Application Data

(60) Provisional application No. 61/650,314, filed on May 22, 2012.

(51) Int. Cl.
*A61N 2/00* (2006.01)
*A61N 2/02* (2006.01)
*A61N 1/40* (2006.01)
*H01F 1/00* (2006.01)

(52) U.S. Cl.
CPC ......... *A61N 2/006* (2013.01); *A61N 1/40* (2013.01); *H01F 1/0045* (2013.01)

(58) Field of Classification Search
CPC ........... A61K 9/14; A61K 9/141; A61K 9/51; A61K 49/1866; A61K 49/1878; A61K 51/1244; A61K 51/1251; H01F 1/0045; H01F 1/0054
See application file for complete search history.

(56) References Cited

U.S. PATENT DOCUMENTS

| | | | |
|---|---|---|---|
| 2003/0028071 A1* | 2/2003 | Handy et al. | 600/12 |
| 2009/0163458 A1* | 6/2009 | Kline | 514/178 |
| 2009/0226521 A1* | 9/2009 | Smyth et al. | 424/484 |
| 2010/0303716 A1* | 12/2010 | Jin et al. | 424/1.11 |
| 2011/0213193 A1* | 9/2011 | Nair et al. | 600/9 |

OTHER PUBLICATIONS

Du et al., "Fabrication, magnetic, and ferroelectric properties of multiferroic BiFeO3 hollow nanoparticles," J. Appl. Phys. 109, 073903, 2011.*
Fiebig, "Revival of the magnetoelectric effect," J. Phys. D: Appl. Phys. 38 (2005) R123-R152.*
Nasrullah, "Shape Engineered Nanoparticle Fabrication for Biomedical Applications," Dissertation Abstract, 2011.*

* cited by examiner

*Primary Examiner* — Charles A Marmor, II
*Assistant Examiner* — Thaddeus Cox
(74) *Attorney, Agent, or Firm* — Marshall, Gerstein & Borun LLP

(57) ABSTRACT

Magneto-electric nanoparticles in a subject interact with an external magnetic field to cause stimulation of neural networks in the subject. Electric signals in the neural network are coupled to magnetic dipoles induced in the nanoparticles to cause changes in electric pulse sequences of the subject's brain.

16 Claims, 4 Drawing Sheets

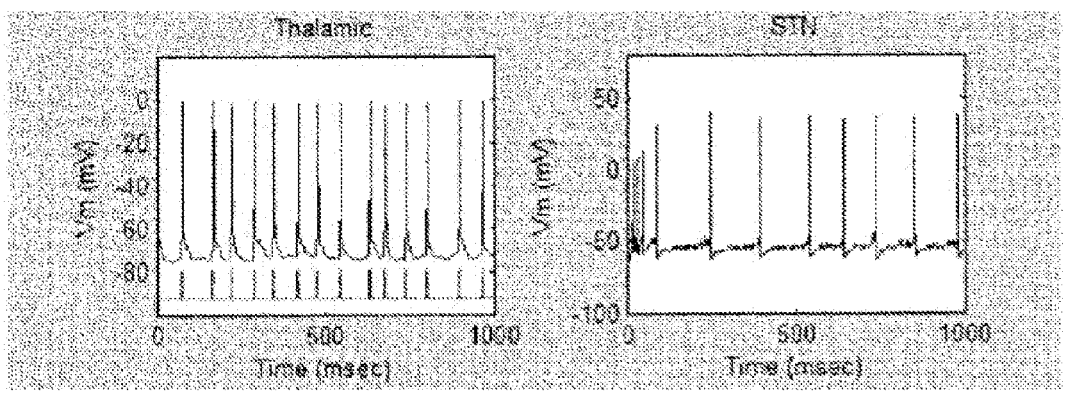
FIG. 1A  FIG. 1B
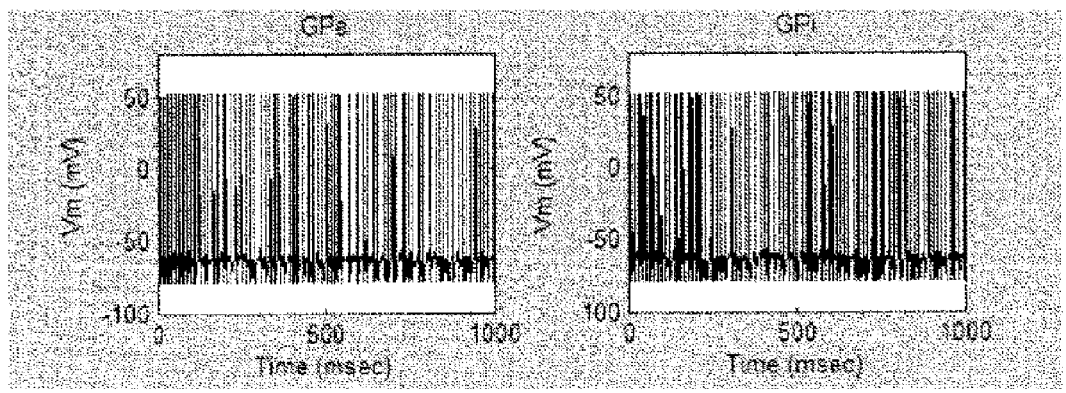
FIG. 1C  FIG. 1D

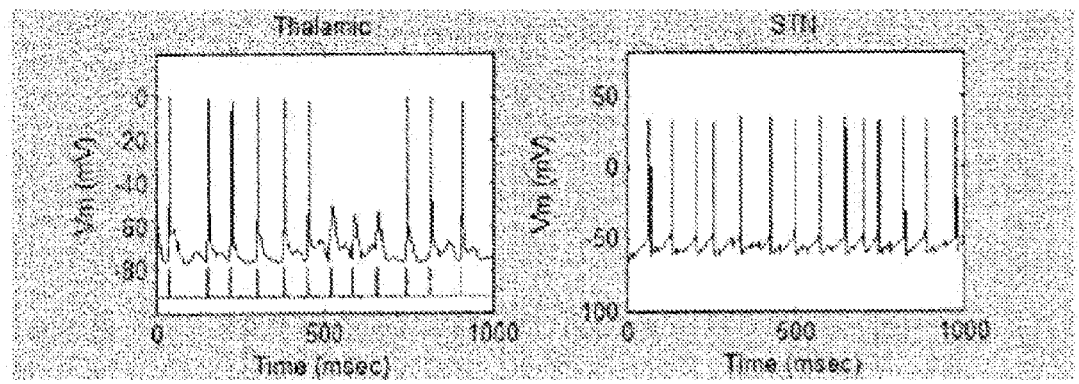
FIG. 2A  FIG. 2B
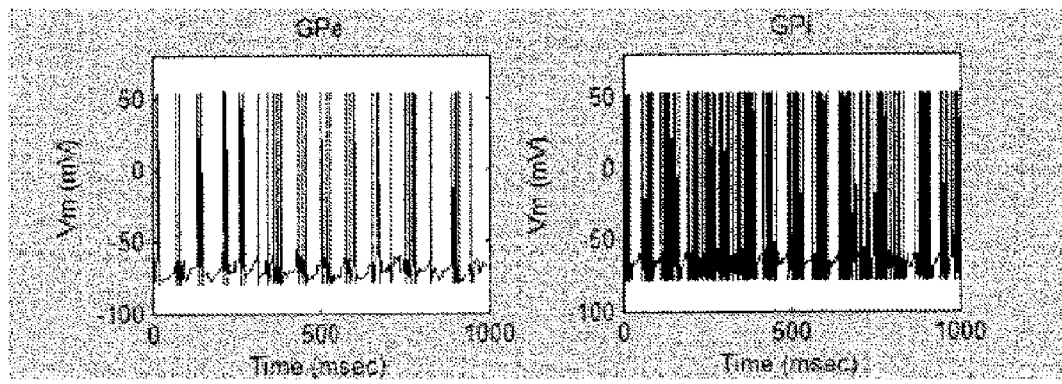
FIG. 2C  FIG. 2D

METHOD FOR NON-INVASIVE BRAIN STIMULATION

CROSS-REFERENCE TO RELATED APPLICATIONS

This applications claims the benefit of priority under 35 U.S.C. §119(e) of U.S. Provisional Patent Application No. 61/650,314, filed May 22, 2012, which is incorporated herein by reference in its entirety and for all purposes.

STATEMENT REGARDING FEDERAL RESEARCH

This invention was made with government support under: Department of Defense (DoD) Defense Microelectronics Activity (DMEA) contract #H94003-09-2-0904; National Science Foundation (NSF) award #005084-002; National Institute of Health (NIH) DA #027049; University of California (UC) Discovery Grant #189573; and Florida Scholars Boost Award #212400105. The government has certain rights in the invention.

FIELD OF THE DISCLOSURE

The present disclosure relates to methods of artificially and non-invasively stimulating neural activity in the brain and, specifically, to methods using magneto-electric nanoparticles.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

The ability to monitor and affect signaling within a neural network and, in particular, within the brain remains an area of research that has broad potential implications in medicine and neural engineering. Within the medical realm, for example, brain stimulation has been shown to relieve and/or prevent symptoms associated with a variety of conditions including, for example, infections, trauma, stroke and other vascular conditions, seizures, tumors, and various neurodegenerative conditions such as Parkinson's disease, Alzheimer's diseases, multiple sclerosis, and others.

The signaling in a biological neural network is based on a highly collective system of electric charges, neurotransmitters and action potentials. The ability to reliably and non-invasively incite and monitor the neuronal charge excitations from outside with the purpose of artificially stimulating the neural network remotely remains an important roadblock to enable advances in the detection, monitoring, and treatment of neurological and related conditions. A neural network can be considered as a complex electrical circuit made of many neurons connected through synapses formed between axons and dendrites. Both types of synapses, known as chemical and electrical synapses, respectively, transfer information between adjacent axons and dendrites directly or indirectly through electric field energy. Consequently, the neural network is sensitive to external electric fields. Moreover, the ability to efficiently control the network at the micro- or nano-scale can enable unprecedented control of important brain functions. Existing technology typically relies on invasive direct-contact-electrode techniques such as Deep Brain Stimulation (DBS), which is one of only a few neurosurgical methods allowed for blinded studies. Existing non-invasive brain stimulation methods include repetitive trans-cranial magnetic stimulation (rTMS) and trans-cranial direct current stimulation (tOCS). rTMS and tDCS represent major advances of the state of the art in non-invasive brain stimulation, but the depth and locality focusing are limited in both methods. In rTMS, high intensity magnetic fields are required to stimulate deep brain regions but high intensity magnetic fields may lead to undesirable side effects.

SUMMARY

In an embodiment, a method of non-invasively stimulating a neural network in a subject brain includes injecting the subject with a solution including nanoparticles formed from a multiferroic material and causing an alternating current magnetic field directed toward the subject to interact with the nanoparticles to induce local electric charge oscillations in the nanoparticles. In some embodiments, the solution is an aqueous solution and, in embodiments, the nanoparticles are magneto-electric nanoparticles. The solution has a concentration of $3 \times 10^6$ nanoparticles per cubic centimeter, in some embodiments. The magnetic field may be directed at a specific region of the subject brain and, in embodiments, the frequency of the magnetic field may be selected according to a frequency associated with electric signals in the specific region of the subject brain. In an embodiment, the frequency is 80 Hz. The nanoparticles are less than 50 nm in size, in embodiments, and are 20 nm in size in some embodiments.

BRIEF DESCRIPTION OF THE DRAWINGS

FIG. 1A illustrates typical electric pulse sequences triggered in the thalamic area of the brain of a healthy person;

FIG. 1B illustrates typical electric pulse sequences triggered in the subthalamic nucleus of the brain of a healthy person;

FIG. 1C illustrates typical electric pulse sequences triggered in the globus pallidus of the brain of a healthy person;

FIG. 1D illustrates typical electric pulse sequences triggered in the medial globus pallidus of the brain of a healthy person;

FIG. 2A illustrates typical electric pulse sequences triggered in the thalamic area of the brain of a person suffering from Parkinson's Disease;

FIG. 2B illustrates typical electric pulse sequences triggered in the subthalamic nucleus of the brain of a person suffering from Parkinson's Disease;

FIG. 2C illustrates typical electric pulse sequences triggered in the globus pallidus of the brain of a person suffering from Parkinson's Disease;

FIG. 2D illustrates typical electric pulse sequences triggered in the medial globus pallidus of the brain of a person suffering from Parkinson's Disease;

DETAILED DESCRIPTION

Figure 3:
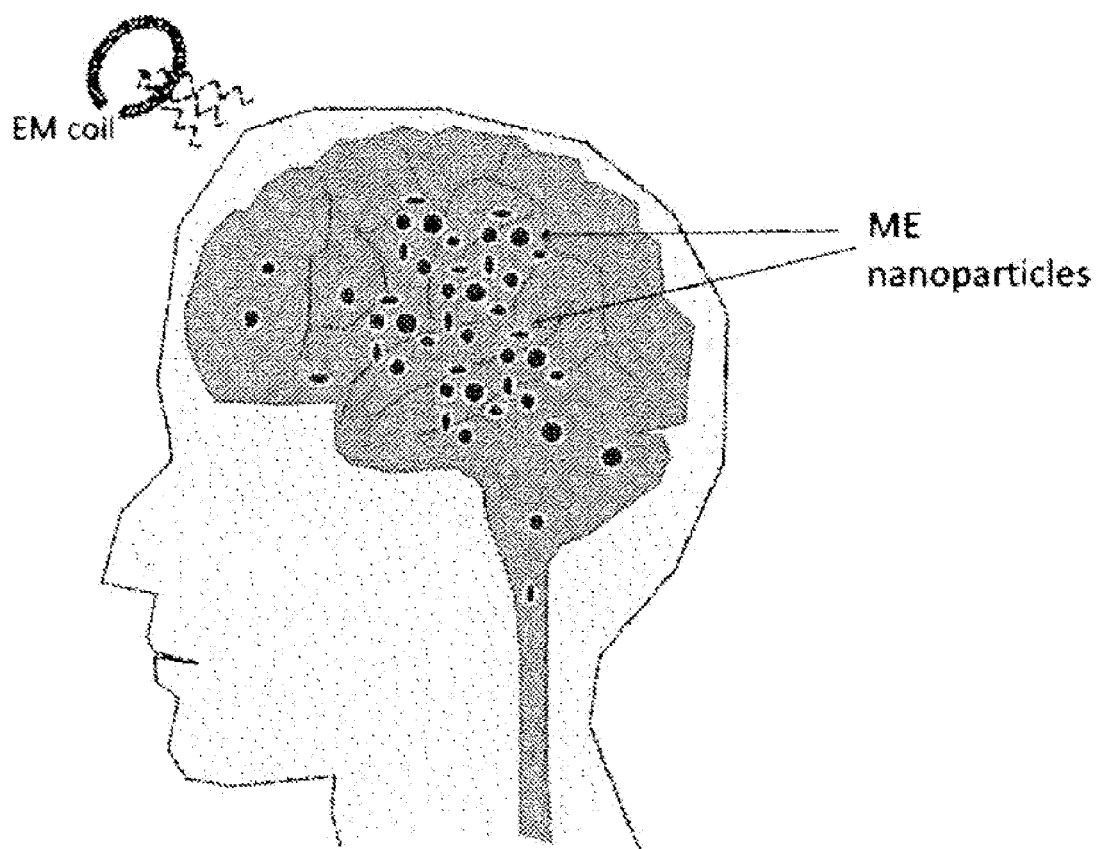
FIG. 3 illustrates the use of an electro-magnetic coil to cause nanoparticles to generate electric fields in a subject brain according to the present description.

A method according to the present disclosure facilitates non-invasive stimulation and/or monitoring of signaling pathways in the brain using magneto-electric (ME) nanoparticles. ME materials include a sub-group of multiferroic materials having the ability to couple magnetic and electric fields at room temperature. In contrast with electric fields, which are surface-limited and typically generated by invasive contact electrodes, magnetic fields generated by ME nanoparticles can penetrate the entire brain non-invasively and be controlled using external low-energy magnetic field sources.

FIGS. 1A-1D illustrate typical electric pulse sequences triggered in four regions of the brain of a healthy person, under normal conditions. FIG. 1A represents the electric pulse sequences generated in the thalamic area. FIG. 1B represents the electric pulse sequences generated in the subthalamic nucleus (STN). FIG. 1C represents the electric pulse sequences generated in the globus pallidus (GPe). FIG. 1D represents the electric pulse sequences generated in the medial globus pallidus (GPi). The four areas of the brain represented in the FIGS. 1A-1D are especially important for understanding different stages of Parkinson's Disease. In a healthy brain, such as that represented by the pulse sequences in FIGS. 1A-1D, the electric pulses are both periodic and uniform in amplitude, and do not display detectable lapses.

By contrast, FIGS. 2A-2D illustrate typical electric pulse sequences triggered in the same four regions of the brain of a person suffering from Parkinson's Disease. In FIGS. 2A-2D, the amplitude and periodicity of each pulse train, relative to those of the corresponding regions in FIGS. 1A-1D, is more or less the same. However, each pulse train represented in FIGS. 2A-2D exhibits pronounced lapses 100 in the periodic sequences. The effect is particularly noticeable in the thalamic region (FIG. 2A).

The methods described herein rely on the presence of ME nanoparticles in the brain. The ME nanoparticles facilitate efficient coupling between magnetic and electric fields at nanoscale (or microscale) over the entire brain volume. Once ME nanoparticles are present in the brain, remotely controlled magnetic fields (as opposed to electric fields) may be used to induce strong local electric charge oscillations in the ME nanoparticles that, consequently, directly interact with the neural network. The interaction between the ME nanoparticles and the neural network can be used to induce localized and targeted brain stimulation. The magnetic fields generated by the ME nanoparticles can effectively penetrate the entire brain (if ME nanoparticles are present throughout the brain) non-invasively. The magnetic fields generated by the ME nanoparticles can be activated and deactivated remotely using external low-energy magnetic field sources such as external electromagnetic coils.

The ME nanoparticles must be manufactured with certain properties for the ME nanoparticles to be effective for use in monitoring or stimulating the neural network of the brain. For example, the ME nanoparticles be small enough to penetrate the blood-brain barrier. In embodiments, the ME nanoparticles are smaller than approximately 50 nm, smaller than 40 nm, smaller than 35 nm, smaller than 30 nm, smaller than 25 nm, smaller than 20 nm, smaller than 15 nm, or smaller than 10 nm. In embodiments, the ME nanoparticles have sizes in a range of 15-20 nm, in a range of 10-20 nm, in a range of 15-25 nm, in a range of 10-50 nm, in a range of 20-50 nm, in a range of 20-40 nm, or in a range of 10-30 nm. In any event, ME nanoparticles small enough to penetrate the blood-brain barrier are able to move into selected brain regions and, accordingly, to effect stimulation or monitoring of said brain regions.

ME nanoparticles may be fabricated by chemical or physical methods, including, but not limited to, thermal decomposition, co-precipitation, and Ion Beam Proximity Lithography (IBPL). In IBPL, for example, a broad beam of energetic (e.g., 20-50 keV) Helium ions illuminates a stencil mask (a thin membrane with etched windows) and the beamlets of transmitted atoms write an array of nanoapertures into resist on a substrate to transfer the mask pattern to the resist. Electrostatic field deflection is used to replicate a sparse stencil mask into a high-density pattern of nanodots. The massively parallel nature of IBPL results in practical throughputs necessary for fabricating large yields of nanoparticles.

Stencil masks with 100×100 $cm^2$ array of 20 nm diameter circular openings with a 5 μm pitch can be fabricated using e-beam lithography. The array of sub-10 nm openings can be used to "write" high-density patterns of nanoparticles to achieve a sub-10 nm linewidth, a 100 nm stencil mask can be coated with a 40 nm scatter layer (e.g., gold) to effectively reduce the size of the stencil openings. Initially collimated atoms impinging on a scatter layer are deflected and trapped within a 0.7 μm thick stencil channel.

In embodiments, the ME nanoparticles are suspended in an aqueous solution and injected into the bloodstream of the patient. Because the ME nanoparticles are small enough to penetrate the blood-brain barrier, the ME nanoparticles are able to move from the blood into the neural tissue of the brain, whereby the ME nanoparticles may be "activated" by an external magnetic field. In embodiments, only a very low intensity external magnetic field is required to stimulate brain activity at any depth in the brain. The external magnetic field generated, for example, by an electromagnetic coil, can be focused to act upon ME nanoparticles in any particular region of the brain, in a manner illustrated generally in FIG. 3. The external magnetic field generates alternating current (AC) signals in ME nanoparticles that are correlated with the frequency spectrum of the neural charge activity, which in turn causes neurons in the region to fire at similar frequencies. For example, provided that the ME nanoparticles have an adequately large magneto-electric coupling coefficient, low-energy magnetic coils can be used to trigger the desired stimulation, as described further below. In an embodiment, the ME nanoparticles have a magneto-electric coupling coefficient of 100 V $cm^{-1}$ $Oe^{-1}$.

The concentration of the solution of ME nanoparticles, and the amplitude and frequency of the external AC magnetic field source, can be varied, in embodiments, to optimally stimulate the neural network. In an embodiment, an external AC magnetic field source generates a field with an amplitude of 300 oersted (Oe), and a frequency variable between 0 and 1 kHz. Generally, the field amplitude should be sufficient to saturate the ME nanoparticles during the stimulation procedure, and the field frequency is selected according to the pulse frequency desired to be generated in the targeted region. In an embodiment, the frequency of the AC magnetic field is 80 Hz.

An aqueous solution of ME nanoparticles has a concentration of between 0 and $10^7$ particles per cubic centimeter, in embodiments and, in an embodiment, has a concentration of approximately $3\times10^6$ particles per cubic centimeter.

Figures 4A, 4B:
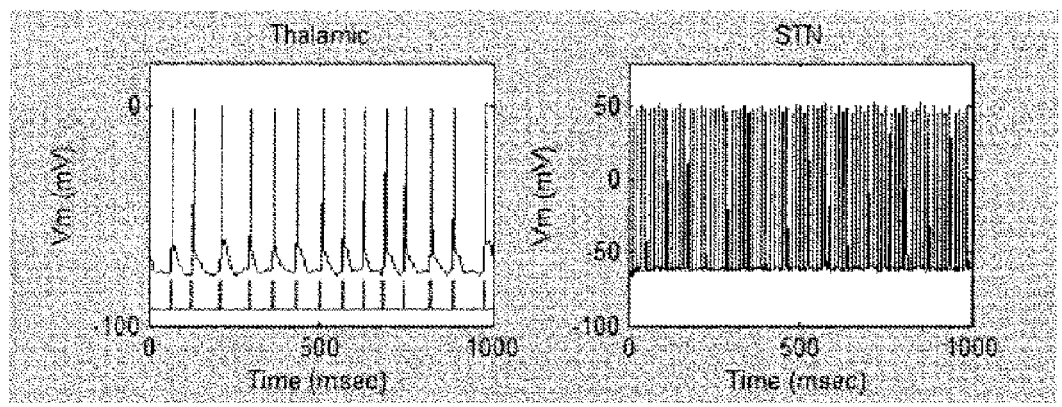
FIG. 4A illustrates modified electric pulse sequences triggered in the thalamic area of the brain of a person suffering from Parkinson's Disease when treated with the present method.
FIG. 4B illustrates modified electric pulse sequences triggered in the subthalamic nucleus of the brain of a person suffering from Parkinson's Disease when treated with the present method.
Figures 4C, 4D:
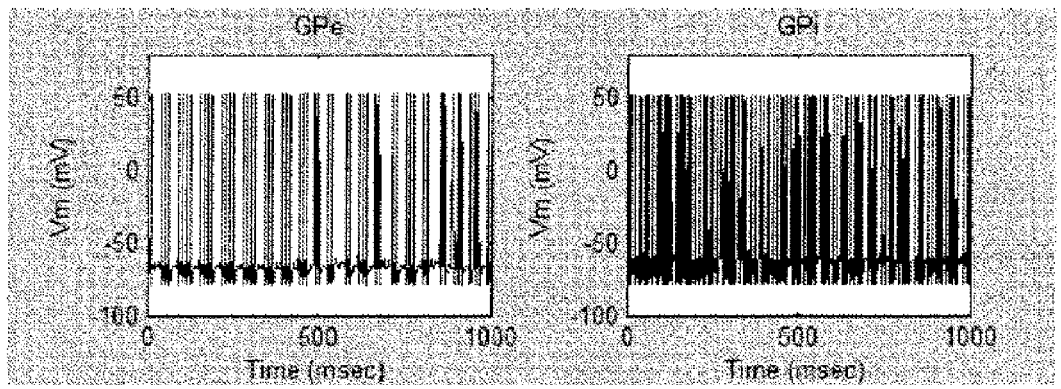
FIG. 4C illustrates modified electric pulse sequences triggered in the globus pallidus of the brain of a person suffering from Parkinson's Disease when treated with the present method.
FIG. 4D illustrates modified electric pulse sequences triggered in the medial globus pallidus of the brain of a person suffering from Parkinson's Disease when treated with the present method.

FIGS. 4A-4D represent electric pulse sequences triggered in the four regions of the brain under study of a patient suffering from Parkinson's Disease after treatment with the ME nanoparticles using a solution having a concentration of $3\times10^6$ particles per cubic centimeter, and a stimulation frequency of 80 Hz (approximately the same frequency as the electric pulse train in the thalamic region of a healthy person (see FIG. 1A). The representation of FIG. 4A illustrates that the most dramatically damaged signals in the Thalamic region are fully recovered, and partial recovery of the periodicity of other brain regions (FIGS. 4B-4D) is also apparent.

Throughout this specification, plural instances may implement components, operations, or structures described as a single instance. Although individual operations of one or more methods are illustrated and described as separate operations, one or more of the individual operations may be performed concurrently and, unless specifically described or otherwise logically required (e.g., a structure must be created before it can be used), nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Upon reading this disclosure, those of skill in the art will appreciate still additional alternative structural and functional designs for a system and a process for identifying terminal road segments through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A method of non-invasively stimulating a neural network in a subject brain, the method comprising:
    injecting the subject with a solution including nanoparticles formed from a multiferroic material; and
    causing an alternating current magnetic field directed toward the subject to interact with the nanoparticles to induce local electric charge oscillations in the nanoparticles, which oscillations interact with the neural network causing neurons in a region of the oscillations to fire at frequencies similar to a frequency of the oscillation.

2. A method according to claim 1, wherein injecting the subject with a solution comprises injecting the subject with an aqueous solution.

3. A method according to claim 1, wherein injecting the subject with a solution including nanoparticles formed from a multiferroic material comprises injecting the subject with a solution including magneto-electric nanoparticles.

4. A method according to claim 1, wherein injecting the subject with a solution including nanoparticles comprises injecting the subject with a solution having a concentration of nanoparticles of $3\times10^6$ nanoparticles per cubic centimeter.

5. A method according to claim 1, wherein causing an alternating current magnetic field directed toward the subject to interact with the nanoparticles comprises generating a magnetic field with an electromagnetic coil.

6. A method according to claim 1, wherein causing an alternating current magnetic field directed toward the subject to interact with the nanoparticles comprises focusing the magnetic field on a specific region of the subject brain.

7. A method according to claim 6, wherein focusing the magnetic field on a specific region of the subject brain comprises focusing the magnetic field on (a) the thalamic area; (b) the subthalamic nucleus; (c) the globus pallidus; or (d) the medial globus pallidus.

8. A method according to claim 7, wherein causing an alternating current magnetic field directed toward the subject to interact with the nanoparticles, further comprises selecting a frequency of the alternating current magnetic field according to a frequency associated with electric signals in the specific region of the subject brain.

9. A method according to claim 1, wherein causing an alternating current magnetic field directed toward the subject to interact with the nanoparticles comprises selecting a frequency of the alternating current magnetic field according to a frequency associated with electric signals in a specific region of the subject brain.

10. A method according to claim 1, wherein causing an alternating current magnetic field directed toward the subject to interact with the nanoparticles comprises causing an alternating current magnetic field having an amplitude of 300 Oe to interact with the nanoparticles.

11. A method according to claim 1, wherein injecting the subject with a solution including nanoparticles comprises injecting the subject with a solution including nanoparticles having a magneto-electric coefficient of 100 V cm$^{-1}$ Oe$^{-1}$.

12. A method according to claim 1, wherein injecting the subject with a solution including nanoparticles comprises injecting the subject with a solution including nanoparticles of 20 nm in size.

13. A method according to claim 1, wherein injecting the subject with a solution including nanoparticles comprises injecting the subject with a solution including nanoparticles less than 50 nm in size.

14. A method according to claim 1, wherein injecting the subject with a solution including nanoparticles comprises injecting the subject with a solution including nanoparticles formed by Ion Beam Proximity Lithography.

15. A method according to claim 1, wherein injecting the subject with a solution including nanoparticles comprises injecting the subject with a solution including nanoparticles comprises injecting a subject having Parkinson's Disease with a solution including nanoparticles.

16. A method according to claim 1, wherein causing an alternating current magnetic field directed toward the subject to interact with the nanoparticles comprises causing an alternating current magnetic field having a frequency of 80 Hz to interact with the nanoparticles.

\* \* \* \* \*